United States Patent [19]

Goldsmith et al.

[11] Patent Number: 4,598,576
[45] Date of Patent: Jul. 8, 1986

[54] FLUID DETECTION DEVICE AND METHOD

[75] Inventors: Alfred D. Goldsmith, Valencia; Roc V. Fleishman, Venice, both of Calif.

[73] Assignee: National Technical Systems, Los Angeles, Calif.

[21] Appl. No.: 624,002

[22] Filed: Jun. 25, 1984

[51] Int. Cl.$^4$ .............................................. G01N 7/10
[52] U.S. Cl. ........................................................ 73/19
[58] Field of Search .................. 73/19, 23, 38, 40.5 R, 73/708, 718, 724; 55/158

[56] References Cited

U.S. PATENT DOCUMENTS

| | | | |
|---|---|---|---|
| 1,016,305 | 2/1912 | Turquand | 73/23 |
| 2,561,414 | 7/1951 | Potts, Jr. | 73/23 |
| 2,811,037 | 10/1957 | Beard | 73/23 |
| 3,559,457 | 2/1971 | Collins | 73/23 |
| 4,056,968 | 11/1977 | Winslow, Jr. | 73/19 |
| 4,096,758 | 6/1978 | Moore | 73/718 |
| 4,208,902 | 6/1980 | Kim et al. | 73/19 |
| 4,357,834 | 11/1982 | Kimura | 73/724 |
| 4,428,776 | 1/1984 | Li | 55/158 |

FOREIGN PATENT DOCUMENTS

1452574 10/1976 United Kingdom .................... 73/19

Primary Examiner—Stephen A. Kreitman
Attorney, Agent, or Firm—Marvin H. Kleinberg

[57] ABSTRACT

A fluid detector device and method capable of detecting the presence of a first fluid such as a gas, which may be mixed with a second fluid, in an external atmosphere where the first fluid is a hydrocarbon gas such as methane or the like, mixed with air, a semi permeable membrane, which extends across an opening of a detection chamber is utilized. Air and the gas have different rates of permeability across the membrane causing a volume change in the chamber. A volume sensitive device signals the presence of the gas. A displaceable element is shiftable in response to the volumetric change in the chamber, allowing the change without significant pressure changes. A capacitive plate can be integral with a displaceable element so that capacitance varies with the change in volume caused by the presence of the gas.

30 Claims, 16 Drawing Figures

FLUID DETECTION DEVICE AND METHOD

BACKGROUND OF THE INVENTION

1. Field of the Invention

This invention relates in general to certain new and useful improvements in fluid composition detectors and method therefor and more particularly, to gaseous fluid detectors and methods which utilize selectively semipermeable membranes to permit differential permeation of fluid across the membrane and which permit continuous monitoring of fluid concentration.

2. Brief Description of the Prior Art

The leakage of fossil fuel gases such as natural gas, primarily methane, from gas meters and gas pipes results in considerable expense to utility companies providing natural gas and to companies piping natural gas and other gaseous products. This considerable expense arises not only from the costs of the gas which is lost through, e.g. pipe and other conduit and equipment, but the necessary repair and replacement costs, false alarms and the like. In addition to the foregoing, sufficiently large gas leaks present other undesirable problems such as safety and health hazards.

It has long been recognized that the development of a relatively low cost gas detector would be highly desirable both as a safety device and as a means for preventing the loss of such gases. Natural gas companies and energy providing utility companies which provide natural gas often use various forms of gas leak detectors. These detectors are generally quite expensive and usually must be constantly adjusted even when routinely examining for gas leaks. Due to the complexity thereof and the costs of manufacture, they are not readily adaptable for home use or use in installations where costs are an important economic consideration.

The typical customer or user of a natural gas product has little or no ability to detect a gas leak, particularly when the gas is methane and is normally odorless and invisible to the naked eye. Usually, in the case of a natural gas, the utility companies add an odoriferous agent, as for example, a mercaptan, to the gas in order to enable the user to smell the presence of the methane. However, even when an odoriferous agent has been added to the gas, the customer or other user of the natural gas typically is not able to smell the same until substantial quantities of the gas have accumulated. At this point, a substantial health and safety hazard already exists.

In addition to the foregoing, many people are not capable of detecting gases, even when containing an odoriferous agent. Further, in many cases, parties working with natural gas, as for example, at transmission stations and power stations, become acustomed to and thereby immune from the smell of small amounts of the gas. Thus, even when the gas has accumulated in substantial quantities, they are incapable of detecting the presence of the gas by smell.

Consequently, a rugged and simple to use, reliable and inexpensive detector of gas, such as methane, and the like for customer use, as well as for use by utility companies and suppliers of gaseous products, would substantially reduce many of the present problems. For example, such a detector would significantly reduce safety and related problems, substantially lower the incidents of false alarms as well as providing more economical transmission and use by the operating companies and the customers.

It has also been recognized that relatively low cost detectors of this type could be used in mining environments, such as in coal mines. In this way, it would be possible to detect the presence of ignitable gases which often accumulate in mines and create very dangerous working conditions. Here again, such a detector must be relatively inexpensive and rugged and highly reliable in its operation. Further, any such gas detector which is reliable and simple to use should be portable so as to be capable of being carried in a pocket of a user. In addition, any such device should have a high degree of sensitivity and must be capable of being easily calibrated. This is particularly true where the gas detector would be used in commercial and industrial environments.

There are presently available flame ionization gas detectors. While these detectors are effective since they have a high degree of sensitivity, in at least parts per million, the cost is quite substantial and may be about two thousand dollars for each such detector. Moreover, these detectors are not necessarily rugged and highly reliable, particularly in industrial and commercial applications. Furthermore, the cost of purchase and maintainence of such units is prohibitive against wide spread use of these detectors.

Recently, there has been provided a gas detector which uses a sintered N-type semiconductor pellet which is essentially comprised of tin oxide and doped with various impurities. A heating coil is embedded at each end of the semiconductor pellet. When a current is passed through one of the coils to heat the pellet and control the temperature thereof, the other coil will serve as an electrical contact for monitoring the electrical conductance of the pellet from coil to coil. Air is absorbed at the surface of the pellet when the sensor is exposed to air and if the air contains a combustible gas, the pellet will react with that gas. The reaction product is absorbed which, in turn, increases the electrical conductance between the two coils. In this way a change in electrical conductance will occur in the pellet when a selected gas is present. While these sintered semiconductor pellet gas detectors may be effective for home use, they are not effective for industrial and commercial purposes. These detectors have a non-linear output which is particularly flat in a range of about 40% to about 60% methane. Further, they are quite difficult to calibrate and consume a substantial amount of power.

There have also been various gas detecting apparatus which utilize a principle of differential diffusion through a porous wall of a vessel in an environment where the vessel may be surrounded by a gas or a mixture of gases which are to be detected. Each of these prior art devices are relatively inefficient either because they are not very responsive, not very accurate or they are too costly to manufacture. More importantly, each of these prior art devices utilize a pressure differential measurement which is inherently inaccurate and do not lend themselves to constant monitoring.

U.S. Pat. No. 4,122,736 to Wheldon et al discloses a device for detecting the presence of a gas contained in a mixture by use of a membrane which is preferentially permeable to that particular gas and which also uses a thin flexible diaphragm. However, the device is constructed so that it is pressure responsive, that is, a pressure differential is created when gas crosses the membrane into a particular chamber. The Wheldon et al device suggests that the flexible diaphragm has a substantial amount of structural integrity. This device, by its very nature and by use of the diaphragm employed, considerably reduces the overall sensitivity and effectiveness of the device and is incapable of continuous monitoring.

U.S. Pat. No. 3,438,241 to McKinley, Jr. also discloses a gas detection system which utilizes a membrane which is selectively permeable to a component of a gas. A carrier gas sweeps the component to a detector and measuring device such as a low volume katharometer.

U.S. Pat. No. 1,016,305 to Turquand et al also discloses a method for using a porous material for an alleged diffusion of gas through the material. The material described in the Turquand et al Patent is porous and the gas will permeate through the porous membrane. The membrane in the Turquand apparatus and method is thus like most prior art apparatus and methods, that is porous, as opposed to being permeable or semi-permeable. Notwithstanding, the Turquand et al Patent also utilizes a pressure differential for measurement of any gas diffusion.

U.S. Pat. No. 3,871,228 to Weiss et al discloses a saturometer which measures a total dissolved gas in a body of water such as a river or a lake, or the like. The Weiss et al patent uses thin wall gas permeable membrane, such as dimethyl silicon tubing. In addition, the Weiss et al patent also relies upon a pressure differential measurement as opposed to a voltage change measurement at constant pressure.

Other patents which relate to the use of differential passage measurement of a gaseous constituent for purposes of measuring the presence of the gaseous constituent include U.S. Pat. No. 2,811,037 to Beard, U.S. Pat. No. 3,546,922 to Dreckmann, U.S. Pat. No. 2,045,379 to Bennett, U.S. Pat. No. 1,746,425 to Heckert and U.S. Pat. No. 2,561,414 to Potts, Jr.

Other devices have been known in the prior art which utilize differential diffusion. One such device is taught in U.S. Pat. No. 1,174,370 to Webster. These devices are relatively inefficient and often totally ineffective. The device in the Webster patent, for example, uses a porous vessel in order to permit the infiltration of the fluid to be detected into the interior of the vessel. Devices utilizing differential diffusion are relatively ineffective due to the inaccuracy of measurement and relatively slow response time.

In each of these prior art devices, there is no means to compensate for external temperature and pressure changes as well as compensating for other constituents contained in the ambient atmosphere which may pass through the porous walls of the detecting chamber. This represents a disadvantage in that there is no means to compare against a standard for absolute measurement.

Many of the prior art devices, as for example, that taught in the aforesaid Turquand U.S. Pat. No. 1,016,305, utilize a porous membrane, as opposed to a permeable for semi-permeable membrane. The use of a porous membrane represents a disadvantage in that the diffusion rates across the membrane are much closer together than those obtained by using a semi-permeable membrane. In addition, prior art devices demonstrate a lack of selectivity, that is, they are not capable of providing a selective diffusion or permeation rate so as to be capable of acurately measuring even small constituent gas changes.

In some of the aforesaid prior art systems for measuring the constituent change in gases, the devices are constructed so that they must necessarily rely upon a pressure change. These prior art devices have typically a slow response time as a result of their large chamber volume with respect to the membrane or porous surface area. They need the large volume to operate their pressure responsive indicator. Consequently, in these prior art devices, not only is the response time slow, but there is always some volume change which interfers with any diffusion or permeating reading. The pressure responsive nature proved to be a disadvantage in these prior art systems in that they were incapable of measuring slow changes. The prior art systems were also essentially insensitive to slow environmental changes.

In addition, and due to the fact some of these prior art systems utilized fairly thick membranes and particularly porous membranes, only a low level signal was achieved, which resulted in some inaccuracy. The fact that all such prior art systems made pressure measurements as opposed to volume change measurements at essentially constant pressure precluded any form of continuous monitoring inasmuch as it was always necessary to reset each such device back to a zero reading before a new reading could be made. In addition, and in many cases, it was necessary to purge the chamber of the prior art systems in order to obtain a true zero reading level before any new measurement or detection was made.

There are also known in the prior art, several capacitive pressure sensors, as for example, those disclosed in U.S. Pat. No. 4,358,814 to Lee et al, the displacement convertor disclosed in U.S. Pat. No. 4,357,834 to Kimura and the pressure-electric transducer disclosed in U.S. Pat. No. 4,096,758 to Moore.

OBJECTS OF THE INVENTION

It is, therefore, a primary object of the present invention to provide a fluid composition detector which uses a selectively semi-permeable membrane to permit differential constituent permeation for enabling continuous constituent monitoring.

It is a further object of the present invention to provide a fluid composition detector which utilizes an effectively sealed chamber to be located in an atmosphere which may contain a gas to be detected and which also includes a membrane providing differential permeability to various gases in the atmosphere permitting two or more of the gases to pass therethrough at different rates.

It is another object of the present invention to provide a gaseous composition detector which uses a membrane having different gas permeability rates for different gases to create a volume change in a detection chamber and where any pressure change is relatively quickly nulled to thereby enable detection of a particular gas.

It is an additional object of the present invention to provide a fluid composition detector of the type stated which automatically calibrates itself at a position of equilibrium to enable repetative or continuous sampling.

It is yet another object of the present invention to provide a detector of the type stated which permits said chamber to have operative pressure communication with the external atmosphere other than through the membrane.

It is also an object of the present invention to provide a method for continuously monitoring the change in constituents of a fluid surrounding a cavity through differential permeation through a membrane wall until the constituent concentrations and fluid pressure are in equilibrium with an external environment.

It is yet another salient object of the present invention to provide a method for detecting the presence of first fluid in admixture with a second fluid by introducing the mixture of fluids into contact with a membrane having different permeability rates for the first and second fluids and allowing the fluids to pass therethrough at different rates of permeation.

With the above and other objects in view, our invention resides in the novel features of form, construction, arrangement and combination of parts presently described and pointed out in the claims.

BRIEF SUMMARY OF THE DISCLOSURE

A fluid composition analyzer and method which comprises one or more chambers which are effectively closed with respect to an outside or external atmosphere or environment. Each chamber has its own internal atmosphere and at least one of these chambers will serve as a primary detection chamber for detection of a first fluid e.g. a gas to be monitored or detected. The detection chamber is provided with at least one selectively semi-permeable membrane to permit differential permeation of the constituents in an external atmosphere or environment through or across the membrane.

The chamber or chambers are effectively enclosed with respect to the external atmosphere although any pressure change in the chambers will quickly null to enable equilibrium conditions with the external atmosphere. Each chamber, however, is expandable or expansible in response to passage of a gas across the membrane to provide a volume change, as hereinafter described.

In a preferred embodiment of the invention, the detector is preferably a gas detector and the first fluid is preferably a gas which is to be monitored and detected and normally carried in or in admixture with a second fluid which is preferably a gas. The second fluid or gas, as for example, air (primarily nitrogen) is normally found in the external atmosphere and may initially comprise the fluid or gas content within the enclosed chamber. This second fluid may contain one or more constituents (first fluid or gas to be detected), as for example, various hydrocarbon gases, e.g. methane which may be in admixture with the air.

A change in the constituents of the air or other external gas in which the detection chamber may be located will enable a differential permeation of the constituents through the membrane resulting in an initial volume change in the chamber. For example, when the chamber contains primarily air as the second fluid and the external atmosphere contains essentially air of the same composition as in the internal chamber, the chamber and the external atmosphere are in equilibrium. If methane or other gas constituent (the first fluid or gas) is introduced into the external air, there will be a differential permeation of the methane through the membrane wall.

The partial pressure of each gaseous component (which is a function of the gas component concentration), constitutes the driving force for moving a gas component through the membrane. This causes an equalizing force causing the partial pressures to equalize. The first fluid (methane) permeates into the enclosed chamber at a faster rate than the nitrogen. This, in turn, causes a small pressure differential which causes a volume change due to the fact that the enclosed chamber is expandable. The amount of volume change is primarily controlled by the concentration differences between the gases inside and outside, the membrane volume and the selectively of membrane which is used.

The membrane is effectively chosen with respect to the external atmosphere and the gas constituents to be detected. When a gaseous constituent permeates across the membrane and causes an initial pressure differential between the external atmosphere and the chamber (usually a pressure increase in the chamber, with respect to the external atmosphere), this pressure differential will immediately drive some element which is moveable or displaceable to cause the volume change. This displaceable or moveable component effectively seals the chamber from the outside environment but is easily moveable in response to the pressure differential to cause a voltage change. Thus, little or no static pressure is required to move the displaceable element, and as the volume increases, the pressure differential decreases until once again there is a pressure equilibrium across the membrane.

Inasmuch as the pressure change is only momentary and small, the device in this sense can be described as having a volume change with no significant pressure change. The pressure change can also be described as "short term" inasmuch as it is designed to permit a resultant volume change and the volume change can be described as "long term".

A transducer, and primarily a volume change transducer, can be connected to the chamber for providing a response to this imbalance and thereby provide an indication of the fluid to be detected. A pressure change indicator would normally measure the pressure change in the chamber as a result of the imbalance caused by differential permeation of the various gaseous constituents. However, since the enclosed chamber is in operative pressure communication with the external atmosphere, as heretofore described, there is no effective pressure differential. The only such change (other than an initial pressure change which nulls quickly) with respect to the detection chamber will be a volume change and the volume change indicator will measure a change of interior volume in the chamber and not a differential pressure between the chamber and the external atmosphere.

The volume change indicator can constitute an extension of the chamber and will be in pressure communication with the external atmosphere so as to eliminate any pressure change transition from affecting the measurement from the volume change. The volume change indicator will thus provide a true volume change measurement as a result of any gaseous constituent being introduced into or removed from the enclosed chamber.

A small bead of liquid in a capillary tube open to one end of the cavity is a highly effective volume change transducer and this bead of liquid is useable, in effect to serve as the moveable element to enable an expansible chamber. Differential pressure indicators, for example, connected between a fixed volume cavity and the external atmosphere will respond to step changes and concentration of a particular constituent by a defined transient response. This response will return to zero differential pressure positions at equilibrium conditions.

The gas composition detector and the method of use thereof is effective in that it enables measurement of a volume change when a gaseous constituent passes across the membrane and into an effectively sealed chamber. In this respect, the chamber is sealed with respect to the external atmosphere, although the gaseous constituent can transfer across the membrane and pressure equalization can be achieved.

The use of a measurement of volume change as opposed to a pressure differential, is highly effective in that it enables a continuous monitoring of the gaseous constituent. When measuring a pressure change, it is necessary to wait for the pressure in the chamber and that of the external atmosphere to reach an equilibrium condition.

After making a gas measurement with the pressure responsive device, it is necessary to effectively purge the chamber from any gas constituent which may again be measured or detected. This is due to the fact that the pressure responsive device always resets itself back to a zero condition or zero reading after making a gas constitutent measurement or detection. Thus, with the pressure responsive device, it is necessary to wait for the device to reset itself back to a zero condition and also to purge the detection chamber.

In the present invention, there is a continuous monitoring in that the device itself is always responsive to and immediately responsive to any change in the constituent concentration and particularly of a gas which is being monitored and detected. The device of the present invention is also effective in that there is a maximum volume displacement and a minimum pressure differential.

In addition to the foregoing, the membrane used in the device and method of the present invention is relatively thin. This use of a relatively thin membrane, as opposed to the relatively thick diaphram or membrane taught in the earlier prior art, permits a much faster response time and is also less expensive to manufacture. Further, the use of the thicker diaphram or membrane type of material used in some of the prior art devices creates a much longer resetting time and this adversely affects the prior art pressure measuring devices.

Changes in the temperature and pressure of the external atmosphere which surrounds the cavity may be communicated to the cavity or chamber through the membrane and thus may cause a response similar to that caused by changes in the constituent concentration. However, compensation is effected by comparing the response of the first cavity with that of another cavity having a different membrane which does not respond to the gaseous constituents in question. The second membrane may have very low permeabilities to the constituents in question or may have substantially identical permeabilities to each of the constituents in question. In a similar way, compensation may be made for temperature and pressure conditions which are external to the cavity.

This invention possesses many other advantages and has other purposes which may be made more clearly apparent from a consideration of the forms in which it may be embodied. These forms are described in detail and form part of the present specification. They will now be described in detail for the purposes of more fully describing the general principles of the invention, but it is to be understood that such detailed descriptions are not to be taken in a limiting sense.

BRIEF DESCRIPTION OF THE DRAWINGS

Having thus described the invention in general terms, reference will now be made to the accompanying drawings in which:

DETAILED DESCRIPTION OF PREFERRED EMBODIMENTS

Figure 1:
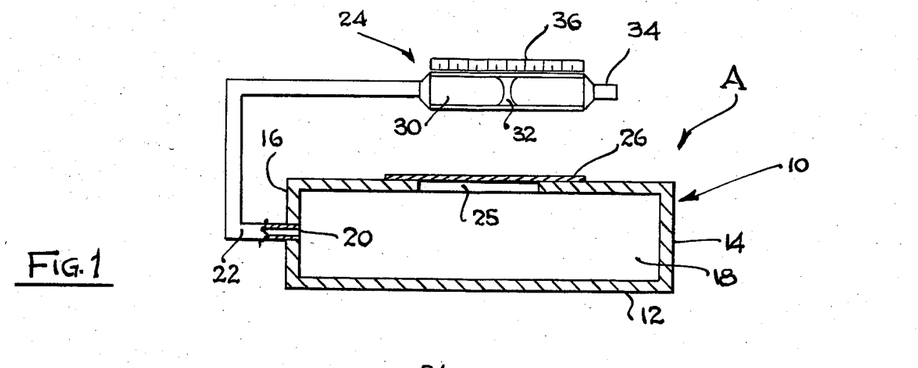
FIG. 1 is a schematic side elevational view partially in section, of a fluid composition detector constructed in accordance with and embodying the present invention.

Referring now in more detail and by reference characters to the drawings which illustrate practical embodiments of the present invention, A designates a fluid composition detector generally comprising an outer housing 10 formed of a material which is relatively non-permeable to gaseous materials. The housing 10 comprises an enclosing side wall 12, one transverse end wall 14 and an opposed transverse end wall 16 and thus forms a generally sealed internal cavity or chamber 18.

The end wall 16 is provided with an aperture 20 for communicating through a conduit or duct 22 to a mechanism 24 which is responsive to a volume change created in the internal cavity 18, as hereinafter described. This mechanism 24 may be a volume change transducer, often referred to as a volume change indicator, as hereinafter described in more detail. However, other than for the aperture 20, the housing 10 forms a completely enclosed cavity 18.

The enclosing side wall 12 of the housing 10 is provided in one region with an opening 25 having a semipermeable membrane 26 extending thereacross and which membrane is also hereinafter described in more detail. The membrane 26 is at least semi-permeable with respect to one or more constituents in the external atmosphere. The membrane 26 must be rigidly supported across the opening of the housing so that there is little or no movement of the membrane, inasmuch as movement of the membrane could interfere with constitutent measurement readings.

The membrane 26 is semi-permeable in the sense that the gaseous constitutents permeate across the membrane by known permeation principles. It is not completely permeable and is not non-permeable. Further, the membrane itself is clearly a non-porous membrane since porous membranes are not preferred in accordance with the present invention.

When the detector device is placed in an external atmosphere which may contain a typical fluid, as for example, air, and when the internal cavity 18 is also filled with air, generally of the same concentration of components and at generally the same pressure and temperature, the internal cavity 18 will be at equilibrium with the external atmosphere. If a second fluid or gas is in admixture with the air, as for example, a hydrocarbon, the membrane is selected so that the hydrocarbon or other gaseous constituent to be monitored and detected will have a different permeability than the normal constituents of the air, namely, oxygen and nitrogen. By selecting the proper type of membrane, it is possible to detect any number of desired constituents.

When there is a gaseous constituent, e.g. methane, in the external atmosphere, the equilibrium between the detection chamber and external atmosphere is upset, and there will be equal but opposite partial pressure drops across the membrane. This will result in a volume change in the contents of the cavity or chamber 18 The methane may have a greater permeability rate across the membrane than does the air. The methane partial pressure differential will drive the methane into the chamber 18 at a much faster rate, thereby causing a net increase in the total gaseous constituents in the chamber 18. It can be observed that as the methane permeates into the chamber, there will be a tendency for the air in the chamber to permeate outwardly into the external atmosphere. However, since the air permeates across the membrane much more slowly, than does the methane, a greater volume of methane will have entered the chamber, than the volume of air which leaves the chamber and there will be an increase in pressure in the chamber which results in the volume increase, as previously described. This volume increase is detected by the means 24 which is responsive to the increase in volume.

The volume change is essentially a function of the rates of permeability of the gas to be detected to the permeability of the other gas in the external environment, as for example, the rate of permeability of methane with respect to air. The speed of the response, e.g. the detection of the volume change is a function of the internal volume of the chamber, as aforesaid, as well as the membrane parameters, for example, the type of membrane, the thickness of the membrane, the surface area and like factors.

The volume change indicator 24 of this embodiment provides the responsive action to the imbalance as a result of differential permeation through the membrane. The volume change indicator may adopt the form illustrated in FIG. 1 and includes a relatively straight horizontally disposed capillary tube 30 having a laterally shiftable bead of oil 32, or other suitable liquid, on the interior thereof. The bead 32 extends across the cross-sectional area of the tube 30 thereby effectively sealing the chamber 18 from an end port 34 in communication with the external atmosphere. In this way, the interior portion of the capillary tube in communication with the cavity 18 is sealed from the external atmosphere. This oil bead also serves as the displaceable element which enables the cavity or chamber 18 to be expansible.

When the pressure in the cavity increases with respect to the outside pressure, the oil bead moves so as to increase the interior volume and quickly reduce any pressure differential between the interior of the cavity and the external atmosphere. The position of the bead provides an indication of the volume change. Thus, this type of transducer is a relatively inexpensive means to measure a volume change. A scale 36 may be located in relation to the capillary tube 30 in order to measure the amount of movement of the oil bead 32. The capillary tube 30 is provided with the opened end 34 in order to permit movement of the bead 32 in response to change of gas constituent volume in the chamber 18 and hence provide a volume displacement measurement.

The phenomenon of gas permeation through a non-porous membrane or through a semi-porous membrane is a complex transfer process and it is believed that a greater appreciation of the principles of the invention will be more fully understood by the following brief description. The permeation of a gaseous constituent through the membrane, which may be a synthetic organic polymer, for example, is promoted by a partial pressure differential between the interior side of the membrane and the exterior side, that is, both the interfaces of the membrane. In the above described embodiment that transfer process is created by a partial pressure differential between the internal cavity and the exterior atmosphere. In essence, the gas effectively dissolves in the membrane at its higher pressure side, as for example, in the case of methane, on the external atmosphere side and passes through the membrane by activated diffusion. The methane degases from the opposite or lower pressure side into the interior of the cavity.

The permeation of methane across the membrane 26 will initially create a pressure build-up in the chamber 18. However, the increase in gaseous constituents and hence, volume of gas in the chamber 18 will push the oil bead 32 to the right, reference being made to FIG. 1, thereby effectively increasing the overall volume of the chamber 18. The bead 32 will stop moving when the pressure on the inside of this chamber is equal to that outside of the chamber, e.g. in the external atmosphere. In this embodiment, the detector 24 includes the displaceable element which permits expansion of the chamber 18. Thus, the detector 24 which permits the volume increase is capable of measuring the increase in volume with respect to or in the chamber 18. Due to the fact that there is a volume change and expansion of the chamber, the pressure differential almost immediately reduces so that there is a pressure equilibrium condition between the inside of the chamber 18 and the external atmosphere.

As indicated previously, this volume change is highly effective in that there is relatively little pressure change throughout the entire system. Moreover, due to the fact that there is a volume change, there is no long length of liquid to move, as in a pressure manometer, or mechanical elements to shift, as for example, as in a pressure gage. Thus, there is relatively little friction in the entire system which could interfere with an accurate volume change reading and hence, an accurate reading of the amount of gaseous constituent which p rmeated into the chamber 18. It can also be understood that the amount or gaseous constituent which permeates into the chamber 18 is a function of the partial pressure of that gaseous constituent, as for example, methane, with respect to the other components in the external atmosphere e.g. nitrogen or oxygen. Thus, the amount of methane which permeates into the chamber is an effective measure of the amount of the partial pressure and hence the amount of the methane in the external atmosphere.

In a pressure detector, the displacement required is minimum. However, in the detector of the invention, maximum displacement is desired for more accurate reading.

The capillary tube 30 which is employed is preferably formed of Teflon, Tygon, or glass. The bead may be formed of various substances, as for example, ethylene glycol, ethyl formamide and the like. A dye, as for example, a red dye may also be incorporated into the bead of material for visability. Further, the tube should have a diameter of about 1 to 2 millimeters and no greater than about 5 millimeters.

Various known membranes can be used in the detector of the present invention. The silicone rubber membranes, such as dimethyl siloxane, are preferred. However, other membranes, as for example, those formed of microporus polypropylene, silicone polycarbonate copolymers and various fluoride silicons are also found to be effective. One of the preferred silicone rubber membranes which may be used in the invention is that silicone rubber membrane marketed by Sandev, Ltd. (a member of Smith & Nephew Associated Companies Group) and is based on a poly(dimethylcyloxane) which contains finely divided silica as a reinforcing fiber. When the rubber is cured, by means of an organic peroxide, it renders a structure consisting of poly(dimethylcyloxane) chains cross-linked by ethylenic bridges, as shown:

This silicone rubber membrane is a thin and highly elastic transparent material having those properties which are desirable for use as a membrane in the present invention.

Inasmuch as the membrane itself may have little or no structural integrity, the membrane itself could be mounted on a suitable backing, such as a porous polysulfone sheet, or the like. In any membrane, it is preferable, although not necessary, to have a tensile strength of at least 200 pounds per square inch and elongation at break point of about 150 percent, an elastic modulus of about 120 pounds per square inch, a burst strength of at least about two pounds per square inch per thousand, and a thickness of no greater than about 0.01 inch.

Figure 2:
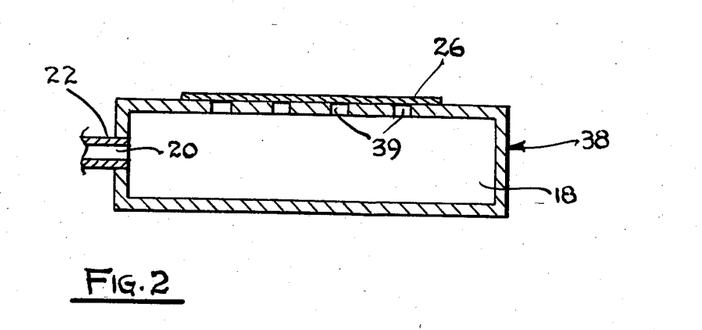
FIG. 2 is a fragmentary schematic side elevation view, partially in section, of a slightly modified fluid composition detector constructed in accordance with and embodying the present invention.

FIG. 2 illustrates a slightly modified form of detector housing 38 which is similar to the previously described detector housing 10. The detector housing 38 includes a plurality of small diameter holes 39, which in combination serve as the opening equivalent to the opening 25 in the housing 10. In this way, the upper wall of the housing 38 provides a fairly rigid support for the membrane 26 which is stretched thereacross. The membrane itself could be adhesively secured to the upper surface of the housing 38 or attached thereto by any suitable means.

Figure 3:
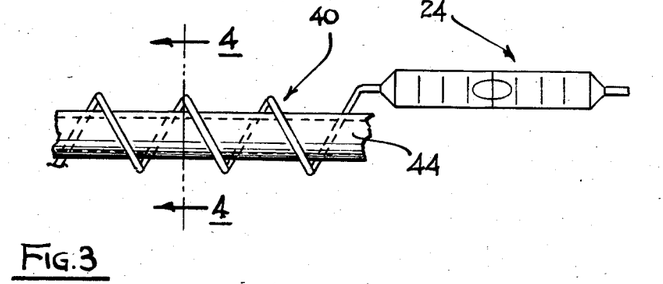
FIG. 3 is a side elevational view of a modified form of fluid composition detector constructed in accordance with and embodying the present invention and shown in relationship to a gas carrying conduit.
Figure 4:
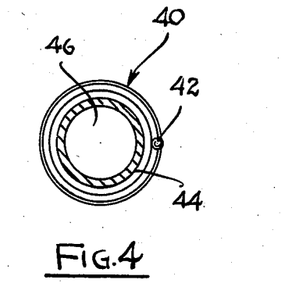
FIG. 4 is a sectional view taken along line 4—4 of FIG. 3.

FIGS. 3 and 4 illustrate a modified form of methane detector 40 which may be constructed in accordance with and embodies the present invention. In this case, the entire membrane is formed of a tubular construction having an interior chamber 42 as shown in FIGS. 3 and 4. One end of the elongate tube may be connected to a volume change indicator 24 similar to that used in the detector A of the invention. In this case, it can be observed that the membrane tube itself can be elongate and wrapped around a pipe or other conduit 44 having an interior bore 46 for carrying a fluid, such as a gas. In this way, it is possible to measure any potential gas leak from the pipe or other conduit 44.

Figure 5:
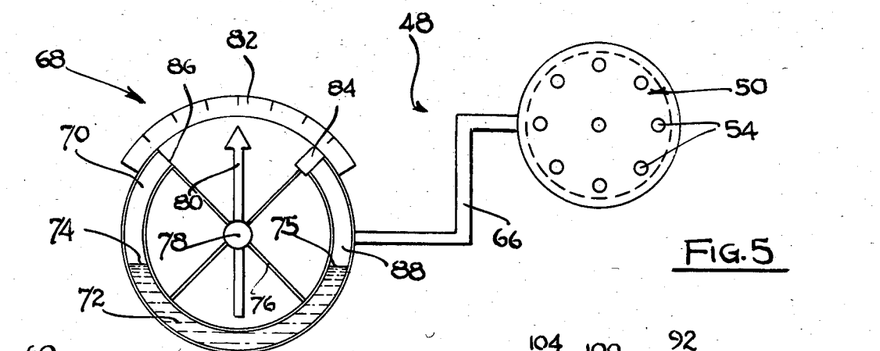
FIG. 5 is a side elevational view of a modified form of fluid composition detector constructed in accordance with and embodying the present invention.
Figure 6:
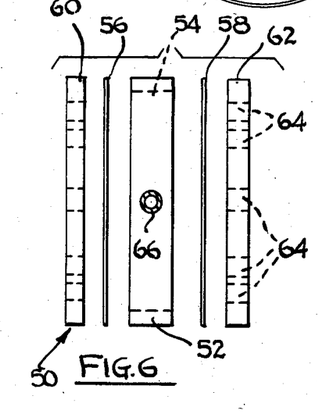
FIG. 6 is an exploded side elevational view of components forming part of detection device of FIG. 5.

FIGS. 5 and 6 illustrate another modified form of methane detector or other gas constituent monitor and detector 48. The detector 48 comprises a detector housing 50 and which is comprised of a main plate 52 having a interior chamber 54 and which is opened on both the upper and lower surfaces thereof, as shown in FIG. 6. Membranes 56 and 58 are disposed on the opposite surfaces of the main plate 52 and enclose the interior chamber 54 of the main plate 52, in the manner as illustrated in FIG. 6. Finally, end plates 60 and 62 having a pattern of suitable apertures 64 hold the membranes 56 and 58 respectively against the main plate 52. In this way, gaseous constituents can pass through the apertures 64 and into the central detection chamber 54. The interior detection chamber 54 thus formed is connected by means of a tube 66 to a volume change indicator 68.

The volume change indicator 68 generally adopts a form of a somewhat U-shaped tube 70, similar to a manometer tube and which includes a body of liquid 72 on the interior thereof presenting upper liquid surfaces 74 and 75. Further, the tube 70 is connected by spokes 76 to a needle bearing 78 permitting rotation of the tube 70. In addition, a pointer 80 is mounted on the needle bearing and is capable of movement with the tube 70. The pointer 80 is movable relative to a scale 82 which is fixed so that rotation of the pointer will provide a volume change indication.

One end of the tube 70 is sealed with a cap 84 and the other end of the tube, namely the end 86 is open. In accordance with this construction, another chamber 88 is formed between the cap 84 and one surface 75 of the liquid, as shown in FIG. 5.

In accordance with the above outlined construction, when there is a permeation of a gaseous constituent, as for example, methane, across the membranes 56 or 58 or both, there will be an initial differential increase in pressure between the chamber 54 and the external atmosphere. This pressure increase would cause a volume change in the chamber 54 which is transmitted to the chamber 88 through the tube 66 which will tend to cause movement of the liquid body 72 so that the right-hand liquid surface 75 would tend to shift downwardly and the left-hand liquid surface 74 would tend to shift upwardly if the tube 70 were fixed. However, since the tube is rotatable the volume change will cause a rotation of the tube 70 in a counter-clockwise direction, reference being made to FIG. 5, in order to correct for the initial pressure imbalance and to achieve a pressure equilibrium condition and this will, in effect, increase the size of the chamber 88. The effective increase in the size of the chamber 88 is proportional to the amount of gaseous constituent which permeated through the membranes 56 and 58 and into the chamber 54. Furthermore, the indicator needle 80 and the scale 82 provide a means of direct read-out of the amount of gaseous constituent which permeated through the membranes 56 and 58 and hence, the relative percentage of this gaseous constituent in the external atmosphere.

It is also possible to mount the pointer or indicator needle 80 on a bimetallic strip (not shown) which is, in turn, secured to the needle bearing or needle pin 78. In this way, automatic temperature compensation can be achieved.

It is also possible to utilize a second rotary indicator with the background scale attached to another gas constituent detector and which is again rotatably mounted. The second detector would constitute a reference detector and could respond to, for example, temperature change, pressure change, humidity variations and the like. Assuming, for example, that the reference chamber was to compensate for water vapor in the air, a membrane would be selected so that the absolute moisture permeability is approximately equal to the permeability of that on the first or measuring detector so there is a matched time response. If the real or measuring detector has a high moisture to air permeability ratio (as is the case for silicone), then the reference membrane should also have a high ratio of permeability of moisture to air or the volume change due to moisture effects will not be effectively tracked. In case of moisture measurement, a three micrometer dimethyl silicon membrane is effective for use and a 0.1 micrometer thick cellulose acetate membrane would be used on the other detector. These two membranes should operate reasonably well to accomplish the desired compensation.

Figure 7:
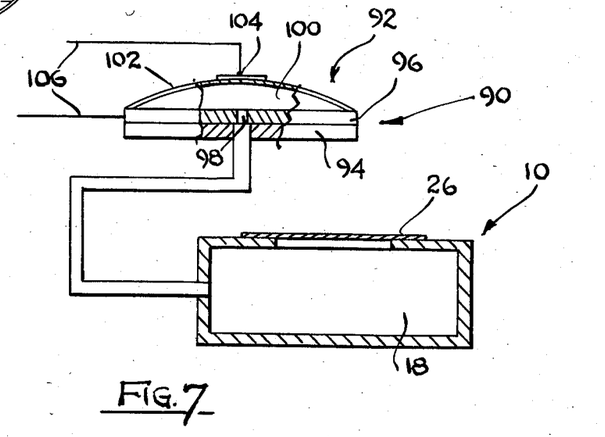
FIG. 7 is a side elevational view, partially broken away and in section, of still a further modified form of fluid composition detector constructed in accordance with and embodying the present invention.

FIG. 7 illustrates still another modified form of gaseous constituent monitor and detector 90 and which includes a housing 10 similar to that in the detector A and this housing 10 is therefore neither illustrated nor described in any further detail herein. In this case, the connecting tube 22 from the housing 10 is connected to a capacitive measuring type volume change indicator 92, as illustrated in FIG. 7. The capacitive type device 92 is only partially schematically illustrated and comprises a base 94 for supporting a first electrical plate 96. In this context, the term "electrical plate" is used to represent one of the capacitive plates forming part of a capacitor. An aperture 98 through the plate 96 and the base 94 permits communication with a capacitor chamber 100. A thin flexible film 102 which may be expandable is sealed to the periphery of either the electrical plate 96 or the base plate 94 in order to insure that the capacitor chamber 100 is completely sealed with respect to the external atmosphere. A second electrical plate, such as a capacitor plate 104 is mounted on the film 102, in the manner as illustrated. Electrical leads 106 are connected to both plates 96 and 94 and to a suitable electrical circuit (not shown) for measuring the change in capacitance as the plate 104 moves relative to the plate 96.

It can be observed that a change in the volume of gaseous constituents in the chamber 18 of the housing 10 of the detector 90 will cause an increase in volume in the capacitor chamber 100. This will result in an upward extension or movement of the film 102 thereby causing a separation between the plates 96 and 104. As a result, there will be a change in capacitance. Further, it can be observed that the capacitance plate 104 serves as the displaceable element relative to the chamber 18. The plate 104 may be relatively thin, such as a metal film, so as to be light in weight and easily moveable.

A suitable electrical circuit, as for example, the circuit hereinafter described, can be used to measure that change in capacitance. This change in capacitance will thereupon provide a direct read-out of the amount of gaseous constituent, such as methane, which permeated across the membrane 26 of the housing 10. It should also be understood, that the capacitor measuring device 90 could also be used with other forms of detector housings, as for example, the detector tube illustrated in FIGS. 3 and 4.

Figure 8:
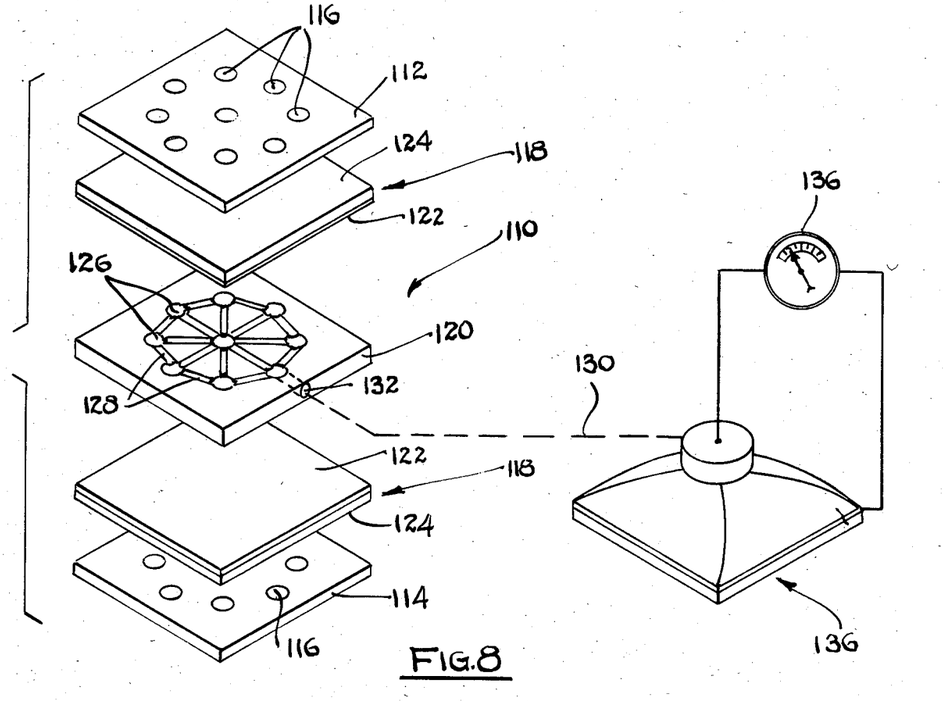
FIG. 8 is an exploded perspective view, showing still another modified form of fluid composition detector constructed in accordance with and embodying the present invention and utilizing a capacitive response device.

FIG. 8 partially schematically illustrates still another modified form of fluid constituent monitor and detector 110. The various plates or segments forming part of the detector are shown in an exploded perspective view, although it should be understood that these various components would be stacked in effective facewise disposition and probably in marginal registration. The detector 110 comprises a pair of outer plates 112 and 114 and each of which are provided with apertures 116 to permit the passage of any gaseous constituent in the external atmosphere. In the embodiment as illustrated, a pair of membrane devices 118 are employed on each of the opposite sides of a base plate 120 which is located in the middle of the structure to be laminated or facewise disposed and connected. Each of the membrane devices 118 include a membrane 122 of the type previously described along with a suitable backing 124. In this case, the backing 124 itself would be porous to any of the gaseous constituents and would not interfere with permeation of the constituents across the membrane 122.

The base plate 120 which serves as a type of housing and support for the other components is provided with a series of apertures 126 which extend therethrough. The apertures on each of the opposite flat faces of the base plate 120 are connected by suitable channels 128 in the manner as shown. In this way, when there is a permeation of gas in the external atmosphere across each of the membrane devices 118, that gaseous constituent will travel through the various apertures 126 which are connected by the channels 128.

A suitable tubing or duct 130 is connected to an aperture 132 in the plate 120 and leads to a capacitive measuring device 134. This capacitive measuring device 134 is similar to the previously described capacitive measuring device 92. Further, in this case, a read-out indicator or guage 136 is connected to leads from the capacitive measuring device 134.

Figures 9, 11:
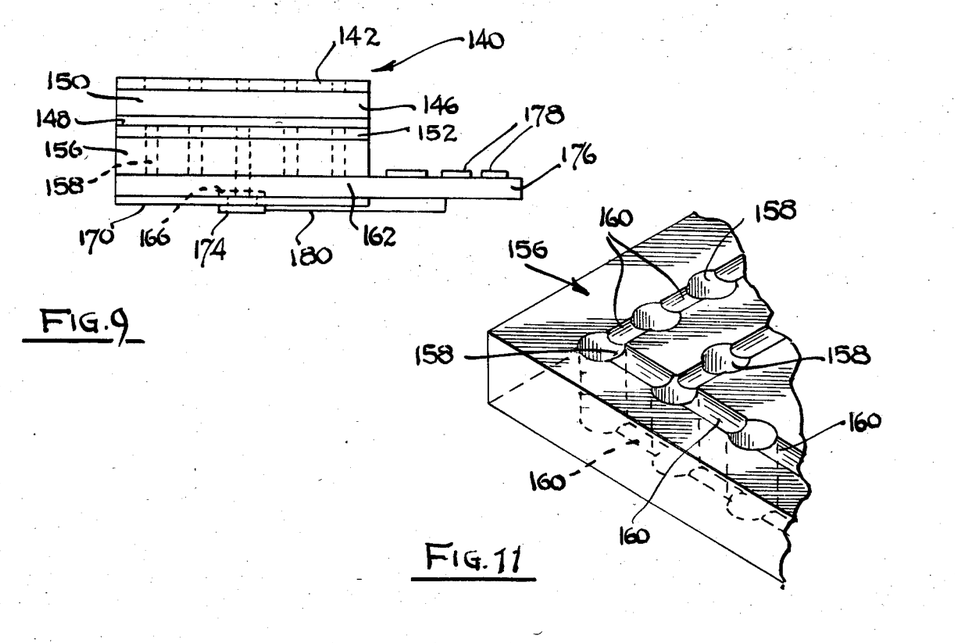
FIG. 9 is a side elevational view, of yet another modified form of fluid composition detector utilizing a capacitive response device.
FIG. 11 is a fragmentary perspective view showing a portion of the base plate forming part of the device of FIGS. 9 and 10.
Figures 10, 15, 16:
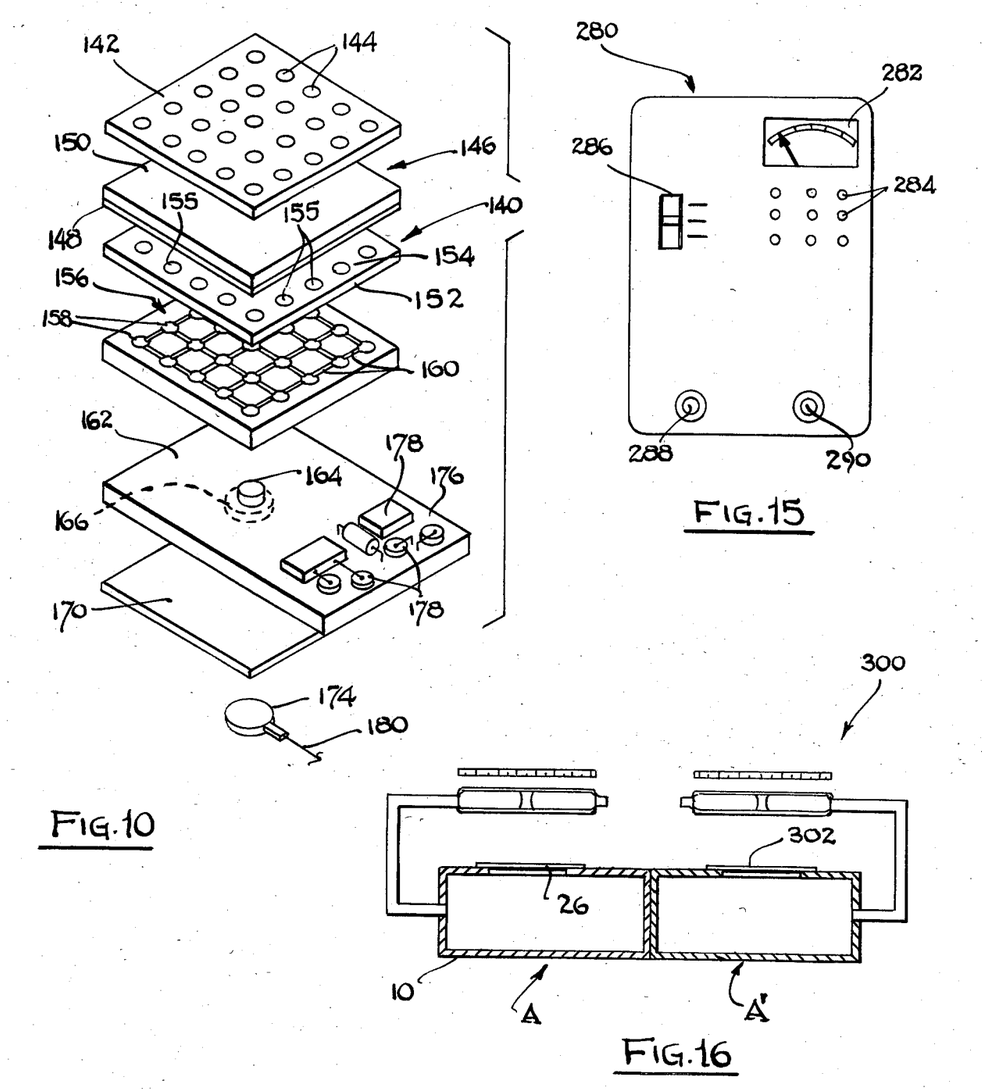
FIG. 10 is an exploded perspective view of some of the components forming part of the device of FIG. 9.
FIG. 15 is a front elevational view of one form of a housing which may be utilized to contain the fluid composition detector of the present invention.
FIG. 16 is a vertical sectional view of still a further embodiment of a fluid composition detector having means for compensating for other gaseous constituents or temperature or pressure change.

FIGS. 9-11 illustrate still another modified form of fluid composition monitor and detector 140 and which is one of the more preferred forms of composition detectors of the invention. This fluid composition monitor and detector 140 is illustrated in the assembled relationship in FIG. 9 and the exploded spaced apart relationship of the various components thereof is shown in FIG. 10.

The detector 140 generally comprises an outer cover plate 142 having a plurality of apertures 144 extending therethrough to permit passage of a gaseous constituent in an external atmosphere. A suitable membrane device 146 comprised of a membrane film 148 and a suitable backing 150 is facewise disposed on the under-surface of the outer cover plate 142. In this case, the membrane 148 is preferably that type of membrane previously described. A porous acrylic or similar sheet 152 having an adhesive coating on each of the flat surfaces thereof, such as the opposed flat surfaces 154, is provided for securing the membrane device 146 to a base plate 156. Any suitable means for securing the membrane device 146 to the base plate 156 could be provided and a separate acrylic sheet 152 is not necessarily required. In any case, the adhesive containing sheet 152 must be pervious to any gaseous constituent passing through the membrane 146 or is provided with apertures 155, as shown.

The base plate 156 is provided with a plurality of apertures 158 extending therethrough from one flat surface to the opposite flat surface. This construction is more fully illustrated in the fragmentary perspective view of FIG. 11. In addition, a plurality of channels 160 connect the various apertures 158 on both of the opposite flat surfaces thereof, also in the manner as illustrated in FIG. 11. The apertures 155 in the acrylic sheet 152 would be aligned with the apertures 158. In this way, there is a relatively uniform distribution of the gaseous constituent passing through the membrane device 146.

Mounted on the underside of the base plate 156 is a first electrical plate 162 which includes an enlarged central aperture 164. Surrounding the aperture 164 on the underside of the electrical plate 162 is a capacitance plate 166 and which capacitance plate 166 is also provided with a central aperture (not shown) to permit the passage of any gaseous constituent therethrough. A somewhat flexible, or otherwise flexible and expandable sheet 170 is secured to the plate 162 around the complete periphery thereof thereby forming an internal chamber. Mounted on the underside of the sheet 170 is a capacitor plate 174 which operates in conjunction with the capacitor plate 166.

The detector of this embodiment of the invention operates much in the same manner as the detector 110 illustrated in FIG. 8. When there is a gaseous constituent, such as methane, contained within the normal ambient atmosphere, the methane will differentially permeate through the membrane 146 and through the apertures 158 in the base plate 156. This methane will also pass through the aperture 164 in the plate 162 and into the chamber between the plate 162 and the film 170. This will cause a volume change in the chamber between the plate 162 and the film 170 thereby causing a movement of the film 170 with resultant separation of the two capacitor plates 166 and 174. This separation can then be electrically processed, as hereinafter described, with an electrical circuit contained on the circuit board 176. A suitable electrical gauge for read-out purposes can be connected to the circuit.

An integrally formed extension on the electrical board 176 contains the electrical circuitry and includes electrical components 178 mounted thereon. Further, the extension 176 could actually contain a printed circuit on the upper surface thereof. In addition, the electrical components 178 which form the electrical circuit are connected to the capacitor plate 166 by an electrical conductor not shown and are connected to the capacitor plate 174 by a wire 180. As an alternative, the electrical plate 162 could be provided with a central recess and the electrical components 178 could be mounted within the recess of the plate 162. In accordance with this construction, the detector is essentially a self-contained unit.

The base plate 156 is preferably formed of a Lexan plastic material and has an overall thickness of about one-sixteenth of an inch. Further, there are preferably about 25 apertures 158 in the plate 156 and each have about a one-fourth inch diameter. The film 170 which is used is preferably formed of that plastic sold under the mark "Saran" and is secured to the underside of the plate 162 along the periphery thereof with a Plybond or other glue. The lower capacitor plate 174 is preferably formed of an aluminum foil and may also be glued to the underside of the film 170.

Figure 12:
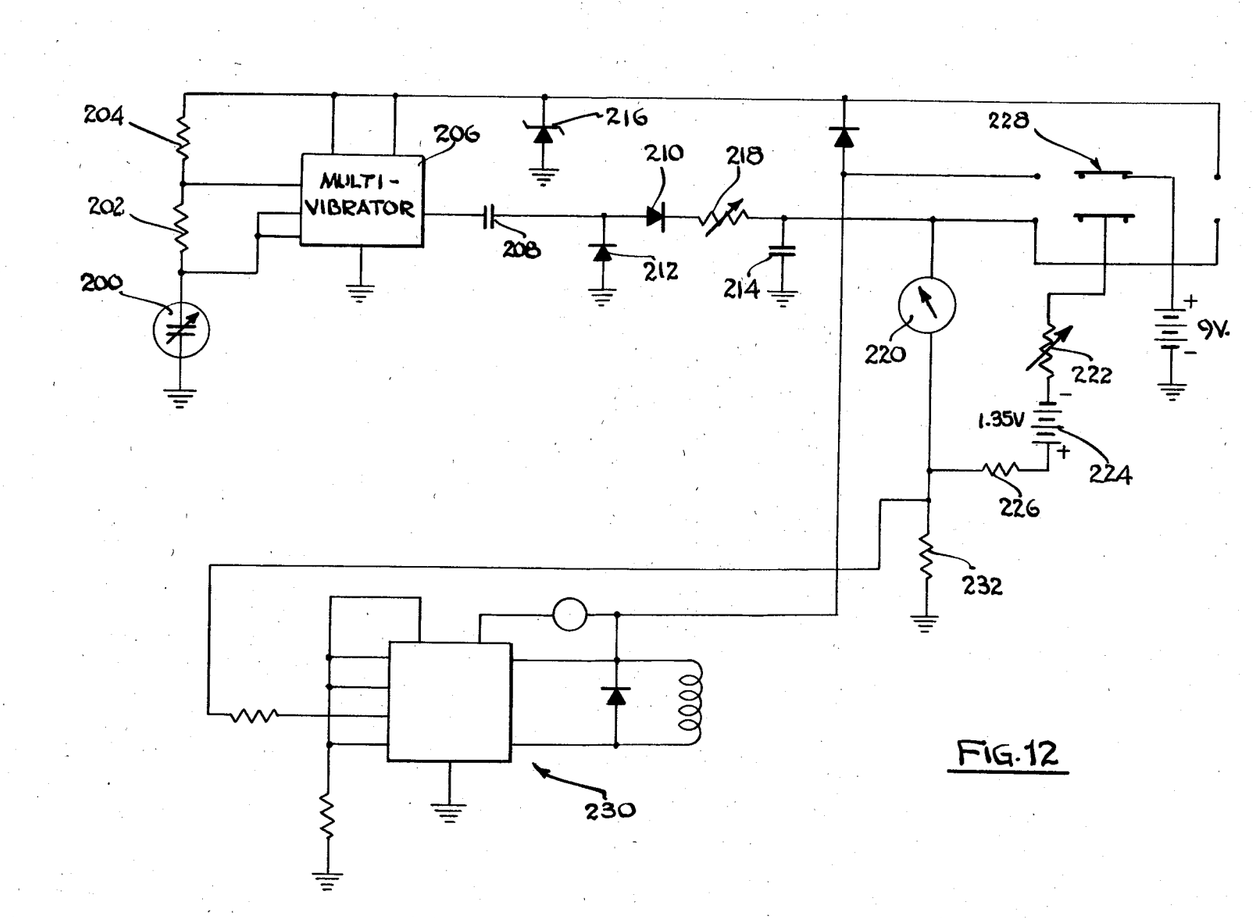
FIG. 12 is a schematic electrical circuit view showing the electrical circuit which may be used with the device of FIGS. 9–11.

FIG. 12 illustrates one form of electrical circuit which is highly effective for use in the detectors of the present invention which include a capacitive response device, as for example, the detectors 90, 110 or 140. The circuit includes a transducer designated by reference numeral 200 along with a voltage dividing pair of resistors 202 and 204. These resistors 202 and 204 are selected to determine the frequency and pulse width of the signal from the transducer 200. In this case, the frequency of the signal is changed by the transducer 200 which is, in effect, a capacitor comprised of a pair of capacitor plates, one of which is shiftable relative to the other, as for example, in the capacitive device 92. Thus, the transducer is actually a variable capacitor and is shown as such in FIG. 12.

The outputs of the transducers 200 and the resistors 202 and 204 are connected to a multi-vibrator 206 which functions as a square wave generator. This square wave generator 206 has an output through a fixed capacitor 208 as, for example, a 0.005 microfarad capacitor. A pair of diodes 210 and 212, which are connected as shown, are designed to effectively short and pass alternate signals from the multi-vibrator 206. In effect, on one half cycle, the diode 212 will permit the passage of the signal and on the other half cycle, the diode 210 will close thereby permitting the shorting of the signal so that it is not transmitted.

A 0.2 microfarad capacitor 214 is connected to the output of the multi-vibrator 206, as shown, and is designed to filter the signal from the multi-vibrator 206 and remove ripples therefrom. In like manner, a Zener diode 216 is provided for voltage regulation and thereby provides stability to the circuit. Located between the diode 210 and the capacitor 214 is a manually adjustable potentiometer 218 which is designed to permit adjustment for the sensitivity of the circuit.

The output signal is then connected to the positive terminal of a gauge 220 for a read-out of the signal itself, and which is, in effect, a read-out of the capacitive change. This capacative change is, in turn, proportional to the amount of separation of the two capacitor plates, as for example, the plates 166 and 174.

A variable resistor or potentiometer 222 and a mercury or other battery source 224 which provides a 1.35 volt power source are designed as a zeroing system. The battery 224 is connected so that it provides a reverse current back toward the multi-vibrator 206. A resistor 226 limits current to prevent premature burnout of the battery 224. In effect, this is a nulling current which thereby permits a nulling of any current passing through the system by the potentiometer 222. It can be observed that there will normally be a continual current flow through the system since the transducer 200 is likely to detect temperature change, minor gas variation and the like in the ambient atmospere.

A three-position switch 228 is provided to turn the device "on" and "off" and also to turn the device "on" with or without a buzzer or other sound generating device, as hereinafter described. In this embodiment, one output of the gauge 220 is connected to a conventional buzzer circuit 230 and circuits of this type are available from National Semiconductor Company of Palo Alto, Calif. as their integrated circuit No. LM322. The buzzer itself is conventional and can be obtained from the Radio Shack Corporation under their model designation No. 273-065. Therefore, neither this buzzer nor the buzzer circuit is described in any further detail herein.

In essence, the circuit of FIG. 12 is unique and also highly effective in the present invention in that it changes the frequency through a fixed capacitor, as for example, the capacitor 208 rather than changing the capacitance through a fixed frequency. In effect, there is a type of measure of a capacitive reactance, as opposed to a measure of pure capacitance. In other words, the transducer is allowed to change the frequency of the oscillator. The current is measured through the fixed capacitor 208 as a function of that frequency established through the transducer 200.

The prior art capacitive measuring circuits use a capacitive transducer as one leg of a negative feedback divider network for controlling an operational amplifier. In this way, the amplifier was controlled so that its gain was directly proportional to the spacing of the plates forming the capacitor. This type of circuit arrangement is more fully exemplified by the Moore U.S. Pat. No. 4,096,758. Another prior art capacitive measuring system used a displacement detector having a variable capacitance which was responsive to the displacement to be measured and a fixed capacitance which was effectively insensitive thereto. A control signal, as for example, generated by an oscillator, is applied to both of these capacitors which yield a difference between the two signals. This difference signal controls the amplitude of the oscillator in such a manner as to keep the control voltage constant. By measuring the signal necessary to keep a constant control voltage, it is possible to thereby determine the distance between the two plates. This type of system is more fully exemplified by the Kimura U.S. Pat. No. 4,357,834.

Figure 13:
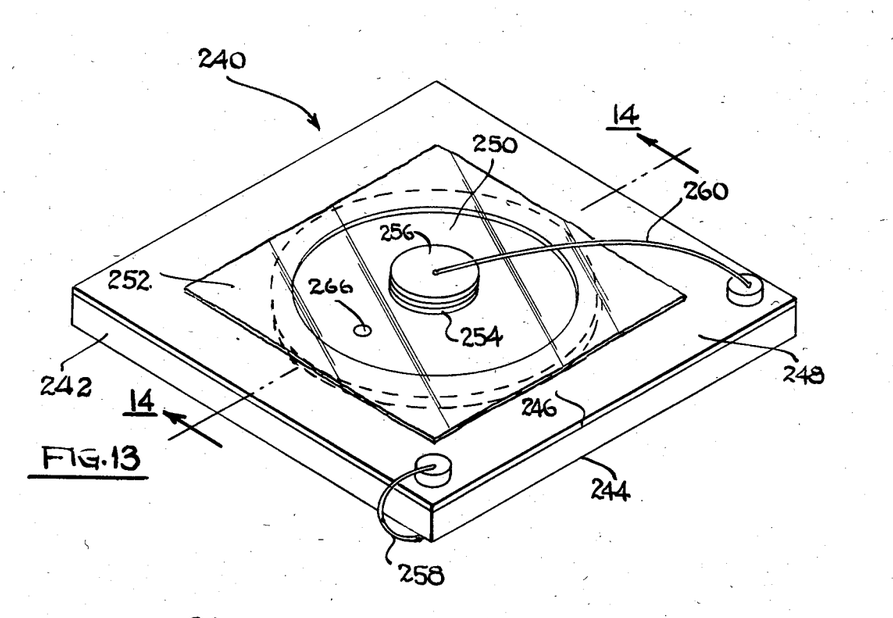
FIG. 13 is a perspective view of yet another modified form of fluid composition detector forming part of and embodying the present invention.
Figure 14:
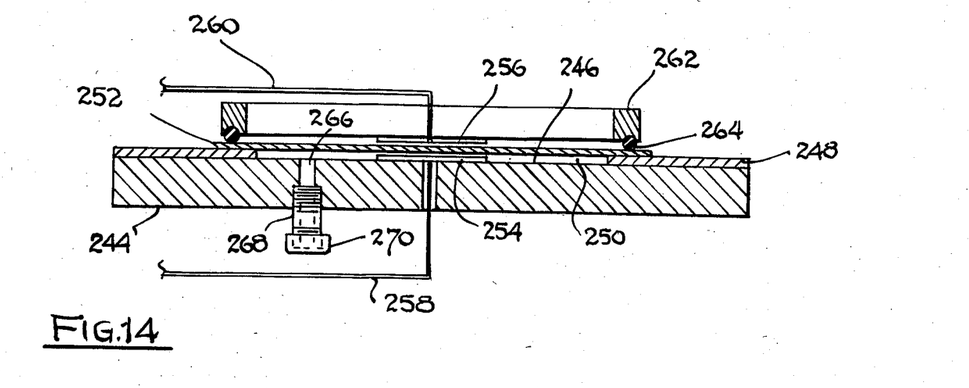
FIG. 14 is a vertical sectional view taken along line 14—14 of FIG. 13 and showing a portion of the fluid composition detector of FIG. 13.

FIGS. 13 and 14 illustrate another modified form of fluid composition detector 240 which comprises a base plate 242 which is provided with relatively flat opposed surfaces 244 and 246, as shown. Mounted on the upper surface 246 is a spacer which may be a simple kraft paper sheet of material 248 and which is provided with an enlarged opening in the manner as shown. This kraft paper may be an adhesive backed paper and preferably has a thickness of approximately three mils. The opening in the kraft paper 248 ultimately provides an interior detection chamber 250 in a manner as hereinafter described in more detail. Disposed over and secured around its complete periphery to the kraft paper layer 248 is a suitable membrane 252 similar to many of the previously described membranes and which preferably has a thickness of about one mil. It can be observed that when the membrane 252 extends over the recess formed in the kraft paper layer 248 the chamber 250 is completely enclosed.

Mounted within the chamber 252 and on the upper surface 246 of the plate 246 is a first capacitor plate 254. Similarly mounted on the upper surface of the membrane 252 is a second capacitor plate 256. Again, these capacitor plates 254 and 256 may be relatively thin metal foil sheets which are light in weight. The lower capacitor plate 254 is connected to a suitable electrical circuit by means of a conductor 258 and the upper capicator plate 256 is similarly connected to that electrical circuit by a conductor 260. The base plate 242 and the kraft paper layer 248 and membrane 252 are all held retentively in engagement by means of a metal O-ring 262 having an annular seal 264 on its undersurface in the manner as shown.

The base plate 242 is also provided with a fluid duct 266 in the manner as shown in FIG. 14 and which is provided with a fitting 268 and a removeable cap 270. A fluid duct 266 is in communication with the detection chamber 250. In this way, the cap 270 can be removed for either purging of the detection chamber 250 and more preferably for permitting a zeroing activity.

The fluid composition detector 240, as illustrated in FIGS. 13 and 14, has been found to be highly effective in that it can be disposed in a small compact unit. Due to the fact that it has very few components, it is light in weight, durable in construction, and can be manufactured at a relatively low cost.

Any of the aforesaid fluid detection devices can be mounted in a suitable housing, as for example, the housing 280 shown in FIG. 15. More specifically, this housing 280 is highly effective to contain the monitoring and detecting device 140, illustrated in FIGS. 9–11, along with the circuit of FIG. 12, or the monitoring and detecting device 240, illustrated in FIGS. 13 and 14. In this case, the housing 280 suitably contains a gauge 282, and which may be equivalent to the gauge 220 in FIG. 12. In like manner, the front face of the housing 280 is provided with a plurality of apertures 284 which would permit the passage of a gaseous constituent. These apertures 284 may be equivalent to those apertures 144 in the plate 142 or may be aligned with the apertures 144 in the plate 142. In addition, the housing 280 would contain a suitable "off-on" switch 286 and, which again, may be equivalent to the switch 228 in the circuit of FIG. 12. Finally, a zero adjust knob 288 and a buzzer threshold control knob 290 may suitably be provided on the front face of the housing 280. In like manner, any other adjustment feature which may be required could be suitably mounted on the front face of the housing 280 for manual control by the operator. The zero adjust control 288 would be suitably connected to the potentiometer 22 in the circuit of FIG. 12. A potentiometer for connection to the buzzer threshold control knob 290 could also be conventionally provided in the buzzer circuit itself.

FIG. 16 illustrates a modified form of fluid composition detector 300 and which may include the fluid detector A illustrated in FIG. 1. Operated in conjunction with the fluid detector A of FIG. 1 is a similar fluid detector A' which is substantially similar in construction and operation to the detector A. However, the detector A' utilizes a different membrane 302. In this way, the membrane 26 in the detector A may be selected for the differential permeation of methane with respect to the normal air constituents. The membrane 26 will have a different permeability than the membrane 302 which may be adapted for the passage of some other constituent in the air. In this way, it is possible to provide a comparison basis. Thus, the detector A' may provide a standard or basis of measurement with respect to any constituent passing through the membrane 26 in the detector A.

As a specific example of the operation of the detectors heretofore described, it may be assumed that the external atmosphere to the detector contains 100 percent nitrogen. In this way, when the detector is initially inserted into the external atmosphere, and opened to the external atmosphere, it will also contain 100 percent nitrogen in the interior chamber thereof. Thus, the detector and the exterior atmosphere will be in equilibrium conditions.

If there is a sudden change in the external atmosphere so that there is now 90 percent nitrogen and 10 percent methane at one atmosphere pressure, the methane will account for one-tenth of the atmosphere. The differential in partial pressure will thereupon drive the methane through the membrane fairly quickly. The methane will permeate into the chamber faster than the nitrogen can permeate out, causing a net gas volume increase in the detector chamber. For dimethyl silicone, for example, the methane permeation rate is approximately four times that of nitrogen. Hence, some nitrogen will exit as the methane enters, yielding a volume change of $$DV = \tfrac{1}{2} VC$$

where C=concentration of methane and Y=interior volume.

The fraction of volume change is a function only of the ratio of the permeability of the gas to be detected to that of a r (or other gas). The response time is a function of the various gas permeabilities, membrane thickness, membrane area, and interior volume, as heretofore described. Since membrane materials can have many orders of magnitude different permeabilities and thicknesses, if the membrane is not selected with relation to the above identified formula the detector may have virtually useless response time, e.g. two days or more. The device of the present invention, with a proper membrane, will, however, almost automatically and very quickly respond to the changes in the external atmosphere and is thus in a position capable of monitoring any further changes.

Thus, there has been illustrated and described a unique and novel fluid monitoring and detecting apparatus which operates on a principal of measuring volume differential when a fluid constituent permeates across a membrane. Thus, the device is capable of continuous monitoring, and the volume change as measured is a linear function of gas composition. The device is thus highly efficient and can be constructed at a relatively low cost. Accordingly, the present invention fulfills all of the objects and advantages sought therefore. It should be understood that many changes, modifications, variations, and other uses and applications will become apparent to those skilled in the art after considering this specification and the accompanying drawings. Therefore, any and all such changes, modifications, variations, and other uses which do not depart from the spirit and scope of the invention are deemed to be covered by the invention which is limited only by the following claims.

Having thus described our invention, what we desire to claim and secure by Letters Patent is:

1. A gas composition detector for continuously monitoring for the presence of and capable of detecting the presence of a first gas component in an external atmosphere on a continuous basis, said detector comprising:
   (a) a sealed chamber having its own internal atmosphere comprised of a gas of predetermined composition therein, said chamber being located in unrestricted communication with the external atmosphere;
   (b) a semi permeable membrane associated with said chamber for permitting passage of the first gas component, whose presence in said external atmosphere is to be detected, across said membrane and into said chamber, said first gas component crossing said membrane having a different rate of permeability than the gas of predetermined composition initially in said chamber;
   (c) displaceable means operatively associated with said chamber, such that passage of the first gas component from said external atmosphere into said chamber causes movement of said displaceable means for changing the volume of said sealed chamber and with essentially no long term pressure change; and
   (d) means responsive to the movement of said displaceable means for providing an indication of the presence of the first gas component in the external atmosphere.

2. The gas composition detector of claim 1 further characterized in that an extension of said sealed chamber permits a change of volume in response to the passage of said first gas component into said sealed chamber across said membrane without creating a pressure differential.

3. The gas composition detector of claim 2 further characterized in that said displaceable means comprises a capillary tube having a small bead of liquid moveable therein in response to changes of volume with respect to said sealed chamber.

4. The gas composition detector of claim 1 further characterized in that the gas of predetermined composition in said sealed chamber is air and said first gas component to be detected is a hydrocarbon.

5. The gas composition detector of claim 4 further characterized in that the hydrocarbon to be detected is methane.

6. The gas composition detector of claim 5 further characterized in that said membrane is a silicone membrane.

7. The gas composition detector of claim 1 further characterized in that the means responsive to the change in volume comprises a movable tube containing a liquid therein and which moves in response to the change of volume, and indicator means moveable to depict a change in volume.

8. The gas composition detector of claim 7 further characterized in that said tube rotates in response to the change in volume and the indicator means is a depicting element which moves in response to movement of said tube.

9. The gas composition detector of claim 1 further characterized in that said detector comprises a second sealed chamber with a membrane different than that associated with said first named chamber, said different membrane having a different permeability than said first named membrane for said first gas component to be detected to thereby provide a reference for comparison.

10. The gas composition detector of claim 9 further characterized in that said different membrane is substantially less permeable to the gas to be detected so as to compensate for temperature difference in the external atmosphere.

11. The gas composition detector of claim 9 further characterized in that said different membrane is permeable to the gas to be detected as well as another gas in admixture therewith.

12. The gas composition detector of claim 1 further characterized in that said detector has one portion which permits said chamber to have pressure communication with said external atmosphere other than through said membrane.

13. The gas composition detector of claim 12 further characterized in that said means responsive to the volume change is a gage having a moveable element therein moveable in response to volume change and where a portion of the moveable element is in communication with said external atmosphere.

14. A gas composition detector for detecting the presence of a gas, said detector comprising:
   (a) a base member having an opening therein;
   (b) a semi-permeable membrane located with respect to and adjacent said base member and permitting a differential permeation of gases thereacross, so that gas permeating through said membrane will pass through the opening in said base member;
   (c) a first electrical plate located on a side of said base member adjacent said membrane;
   (d) a first electrical contact connected to said first electrical plate;
   (e) a second electrical plate located with respect to said first electrical plate mounted on a flexible member which is movable relative to said first electrical plate to form a chamber creating an expandible volume therebetween so that one of said plates is freely movable relative to the other in response to a permeation of gas across said membrane;
   (f) a second electrical contact connected to said second electrical plate;
   (g) electrical circuit means connected with respect to said contacts responsive to capacitive reactance when one of said electrical plates is moved relative to the other for generating a signal in reaponse to that movement and the resultant change in capacitive reactance; and
   (h) indicator means responsive to said signal to provide an indication of the gas permeating across said membrane.

15. The gas composition detector of claim 14 further characterized in that said membrane and first electrical plates are effectively sealed with respect to said base member so that a gas permeating across said membrane will pass through at least one aperture in said base member.

16. The gas composition detector of claim 14 further characterized in that said base member has a plurality of apertures therein to permit passage of a gas.

17. The gas composition detector of claim 14 further characterized in that said first electrical plate is fixed and said second electrical plate is movable relative to the first electrical plate.

18. The gas composition detector of claim 17 further characterized in that said first electrical plate comprises a circuit board.

19. The gas composition detector of claim 17 further characterized in that said gas to be detected is a hydrocarbon.

20. The gas composition detector of claim 19 further characterized in that said gas to be detected is methane.

21. The gas composition detector of claim 20 further characterized in that said membrane is a silicone membrane.

22. The method of claim 21 further characterized in that said membrane is a silicone membrane.

23. A method for the detection of a first fluid which may be in admixture with a second fluid, said method comprising:
   (a) introducing a sealed chamber into an environment containing the second fluid and which may contain the first fluid to be detected,
   (b) allowing any first fluid in the environment to permeate through a membrane associated with said chamber and which membrane is substantially more permeable to the first fluid then to the second fluid thereby causing an increase in the volume of fluid in the chamber without any substantial pressure change between said chamber and the environment, and
   (c) generating a responsive action based on the change of volume of fluids in said chamber to provide indication of the presence of said first fluid.

24. The method of claim 23 further characterized in that said first and second fluids are each gases.

25. The method of claim 24 further characterized in that said first gas is a hydrocarbon and said second gas is air.

26. The method of claim 24 further characterized in that said first gas is methane and said second gas is air.

27. The method of claim 23 further characterized in that said method comprises measuring a differential volume of another fluid in admixture with the first and second fluids across another membrane having a different permeability than the first named membrane.

28. A gas composition detector for continuously monitoring for the presence of and capable of detecting the presence of a first gas component in an atmosphere on a continuous basis, said detector comprising:
   a first chamber including, as one bounding surface thereof, a semi-permeable membrane fixedly mounted to a relatively inflexible porous substrate, said membrane having greater permeability for preselected gases whose presence in tan atmosphere is to be detected and signalled;
   said first chamber further including freely movable means for determining the volume of said first chamber;
   transducing means responsive to changes in volume in said first chamber for signalling such volumetric changes;
   whereby the presence of preselected gases in an atmosphere is detected and signalled by the change in volume resulting from the differential permeation of said membrane by said preselected gases from a contaminated atmosphere exterior to said first chamber into a controlled atmosphere within the interior of said first chamber.

29. A gas composition detector for continuously monitoring for the presence of and capable of detecting the presence of a first gas component in an atmosphere on a continuous basis, said detector comprising:
- a chamber having a wall portion including a semi-permeable membrane immovably bonded to a rigid porous substrate to permit permeation of an enclosed atmosphere containing a gas mixture by a first gaseous component whose presence in an external atmosphere of a similar gas mixture is to be detected and signalled;
- volume expansion means operatively involved with said chamber including flexible surface means to permit unrestricted volumetric expansion without changes in pressure;
- signalling means including transducing means responsive to volumetric changes for generating a signal corresponding to and representative of the concentration of the first gas component in the atmosphere external to said chamber.

30. A gas composition detector for continuously monitoring for the presence of and capable of detecting the presence of a first gas component in an atmosphere on a continuous basis, said detector comprising:
- first chamber including interconnected collecting passages in pressure equilibrium with external atmosphere;
- a membrane for selectively detecting the first gas component in said first chamber;
- volume expansion means coupled to said collection passages and including transducer means for detecting and signalling volumetric expansion resulting from differential permeation of said membrane by the first gas component.

* * * * *